United States Patent [19]

Polyak et al.

[11] Patent Number: 5,010,882
[45] Date of Patent: Apr. 30, 1991

[54] IMPLANTABLE PENILE PROSTHESIS

[75] Inventors: Mark Polyak, Minnetonka; Robert W. Pugh, Jr., Lakeville, both of Minn.

[73] Assignee: American Medical Systems, Inc., Minnetonka, Minn.

[21] Appl. No.: 435,641

[22] Filed: Nov. 13, 1989

[51] Int. Cl.$^5$ .............................................. A61F 2/26
[52] U.S. Cl. ................................................... 128/79
[58] Field of Search ...................... 137/624.11, 624.14; 251/61.4; 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,256,093 | 3/1981 | Helms et al. | 128/346 |
| 4,267,829 | 5/1981 | Burton et al. | 128/79 |
| 4,318,396 | 3/1982 | Finney | 128/79 |
| 4,353,360 | 10/1982 | Finney et al. | 128/79 |
| 4,369,771 | 1/1983 | Trick | 128/79 |
| 4,378,792 | 4/1983 | Finney | 128/79 |
| 4,399,811 | 8/1983 | Finney et al. | 128/79 |
| 4,407,278 | 10/1983 | Burton et al. | 128/79 |
| 4,412,530 | 11/1983 | Burton | 128/346 |
| 4,457,335 | 7/1984 | Trick | 137/522 |
| 4,590,927 | 5/1986 | Porter et al. | 128/79 |
| 4,622,958 | 11/1986 | Finney | 128/79 |
| 4,679,546 | 7/1987 | van Waalwijk van Doorn et al. | 128/DIG. 25 |
| 4,682,589 | 7/1987 | Finney | 128/79 |
| 4,773,403 | 9/1988 | Daly | 128/79 |
| 4,791,917 | 12/1988 | Finney | 128/79 |

FOREIGN PATENT DOCUMENTS

584540 1/1947 United Kingdom ........... 137/624.14

Primary Examiner—Cary E. Stone
Attorney, Agent, or Firm—Peter C. Richardson; Lawrence C. Akers; Michael J. Pantuliano

[57] ABSTRACT

A penile prosthesis implantable within the corpus cavernosum of the penis in order to alleviate erectile impotency includes a unique deflation valve mechanism for returning the prosthesis from the erect to the flaccid state. In its preferred embodiment the prosthesis is of a unitary type comprising a distal portion including a pump, a medial portion defining a pressurizable chamber comprising an internal, tubular, substantially non-distensible portion and a concentric tubular sleeve, and a proximal portion including a fluid reservoir, the latter being in fluid communication with the pump. The deflation valve mechanism is activated in accordance with pressure differential conditions within the valve and a movable or distensible partition capable of exerting an internal force within the valve to place the valve in an open mode, thereby effecting the deflation of the prosthesis or hydraulic system in which the valve mechanism is present. Apparatus for extending the length of the prosthesis are also provided.

30 Claims, 3 Drawing Sheets

IMPLANTABLE PENILE PROSTHESIS

BACKGROUND OF THE INVENTION

This invention relates generally to the field of implantable prosthetic systems for overcoming male erectile impotence, to a method therefore, and more specifically to prosthetic devices particularly of the unitary type. It also relates to a unique deflation valve for use in such prosthetic devices and in hydraulic systems.

A number of devices are available for enabling those with erectile impotency to achieve an erection. These devices are generally implanted within the corpus cavernosum of the penis. Normally two such devices are utilized, one implanted into each corpus cavernosum. Generally speaking, the penile prostheses which are available, or which have been described, include a reservoir, a pump and a pressure chamber. Fluid is pumped from the reservoir by the pump to the pressure chamber to achieve an erection. Illustrative of the early devices are those disclosed in U.S. Pat. No. 3,853,122 to Strauch, et al, which discloses an external pump and a single tube and valve mechanism, and U.S. Pat. No. 3,954,102 to Buuck, et al which discloses a device manually operated through the use of bypass valve means.

A penile prosthesis using an inflatable hinge is described in U.S. Pat. No. 4,267,829 to Burton and Mikulich. In this patent, a tubular section includes a chamber which undergoes only a small change in volume and therefore requires minimum fluid displacement as the prosthesis transforms from a non-erect to an erect condition. Unitary penile prostheses which include a pair of concentric chambers, one of which is pressurized, are disclosed in U.S. Pat. Nos. 4,353,360 and 4,399,811. In these patents, the inner of two concentric chambers is pressurized while the outer of the two chambers acts as the fluid reservoir prior to erection. To attain an erection, fluid is pumped from the outer reservoir through a pump to the inner reservoir. Thus, the total volume of the two chambers is always constant.

Further illustrative of the devices available is that disclosed in U.S. Pat. No. 4,590,927 to Porter and Kuyaya. This patent relates to a unitary penile prosthesis which comprises a tubular enclosure having a distal portion which includes a pump, a medial portion including a pressurizable chamber which contains an internal tubular, substantially non-distensible portion and a concentric tubular sleeve, and a proximal portion defining a fluid reservoir therewithin. The non-distensible portion of the pressurizable chamber is typically crimped so that it may expand in diameter. The tubular sleeve may elastically bias the non-distensible portion to its flaccid state. A passageway fluidically connects the reservoir and the pump and is in fluid isolation from the pressurizable chamber of the medial portion.

In all of the devices available or described a need has remained for an improved means for effecting a sure and quick means for deflating the device from the erect to the flaccid state. The manual compression of suitable valve means which is the typical method of deflating the erect prosthesis of the known or described prosthetic devices has the problem of requiring a rather inexact determination by the user as to the location of the deflating valve. It is thus apparent that a prosthetic device which would provide a sure, facile and quick means for effectively deflating the penile device so as to return said device from its erect to flaccid state would be very desirable.

SUMMARY OF THE INVENTION

The present invention relates to penile prosthetic devices which are implantable within at least one corpus cavernosum of the penis, each of said devices including an implantable broadly tubular enclosure having a generally tubular pressurizable chamber section defined therewithin which is expandable from a flaccid to an erect state. The devices of this invention are further characterized by an improved means for returning said enclosure from the erect to the flaccid state, said means comprising a unique valve mechanism which is in fluid communication with said pressurizable chamber section and with a fluid reservoir.

In its broadest context, the valve mechanism includes closure means for normally keeping the valve in a closed mode, means for time-deferring the transfer of fluids within the valve, and a movable partition or impacting means disposed in proximity to the closure means capable of impacting upon the latter. In operation, a change in the internal fluid pressure conditions of the valve will occur as a consequence of the time-deferred transfer of fluids. As a consequence, such change in internal pressure conditions can cause the movable or distensible partition or impacting means to impact upon the closure means with sufficient force to cause the valve to open.

The valve mechanism of this invention preferably comprises a housing having closure means defined therewithin, the closure means being a poppet and including means for exerting a force upon the head of the poppet for normally keeping the sealing edge thereof in sealing contact with the inner surface of said housing, the poppet head also being disposed within a fluid-containing chamber the pressure of which, in addition to the means for exerting a force upon the poppet head, normally keeping the closure means and thus the valve mechanism in a closed mode. The valve mechanism further contains a movable or distensible partition capable of impacting upon the poppet and a further chamber adjacent to the distensible partition, the latter chamber being in fluid communication with the chamber disposed about the poppet head through means which time-defer the transfer of fluid between said chambers. As a consequence precalculated pressure conditions can be established so that fluid pressure in the chamber adjacent to the partition can exert sufficient force upon the partition to cause the latter to impact upon the poppet and break the sealing contact of the poppet with the housing, thereby opening the valve mechanism and permitting the flow of fluid from the stiff, erect chamber section to the reservoir. As a consequence the chamber section and the prosthetic device are deflated.

The preferred penile prosthesis of this invention is of a unitary type in which the pressurizable chamber section is defined medially within the implantable tubular enclosure between a front section which is adapted to be disposed inside the distal portion of a patient's penis, and a rearward section adapted to be implanted within the root end of the penis. In a further preferred embodiment, the front section is elongated and is substantially rigid and contains a bulb pump, and the rearward section contains a fluid reservoir. The pressurizable section also preferentially includes a substantially non-distensible tubular portion and a tubular sleeve concentric with said tubular portion, said tubular portion being expandable from a flaccid to an erect, stiff state when the interior volume thereof is filled substantially to capacity. In this embodiment both the reservoir and pump are in series along the length of the tubular enclosure with respect to the chamber section. The reservoir is adapted to hold a substantial portion of the fluid needed to transform the tubular portion of the pressurizable chamber section from its flaccid to its erect state, and the pump is adapted to be in fluid communication with the chamber section. A passageway is also provided which fluidically connects the reservoir and pump but which is in fluid isolation from the pressurizable chamber.

In addition to simplifying and improving deflation, the preferred device of this invention also provides the improved ability to lengthen the device according to need and also serves to have an improved means for preventing spontaneous deflation or inflation and for improving flaccidity.

DETAILED DESCRIPTION OF THE DRAWINGS

Figure 1:
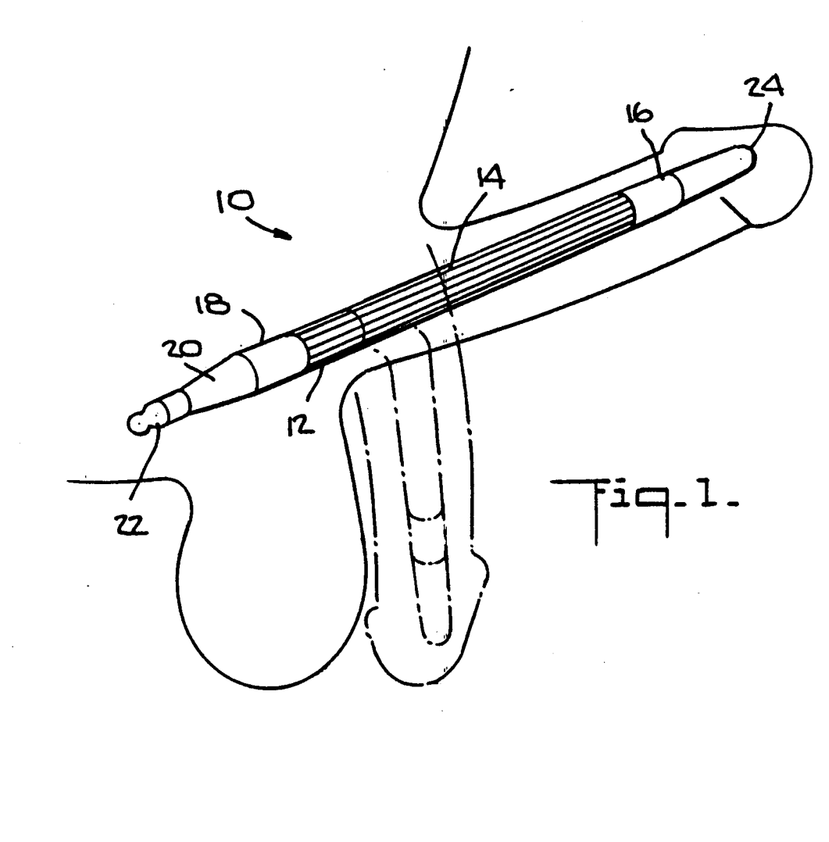
FIG. 1 is a side elevational view of a typical prosthesis of the subject invention in its implanted state depicted in both its erect and flaccid states.

Referring to the drawings wherein like reference characters are utilized for like parts throughout the several views, an inflatable penile prosthetic device 10 of the unitary type is shown in FIG. 1. It comprises an implantable device sized to be implanted within one corpus cavernosum of the penis. Normally two of such broadly tubular unitary devices of the kind shown in FIG. 1 are implanted, one in each corpus cavernosum. However, if desired a single prosthesis could be employed. While the unitary type of implant is preferred, the prosthesis of the present invention can also be of the non-unitary type wherein, for example, the fluid reservoir can be disposed separate from the other sections of the prosthesis.

In the prosthesis defined by FIG. 1, the outer layer of the device 10 is composed of a material which is physiologically inert or biocompatible. Illustrative of such material is silicon rubber, but any material known to be useful for artificial devices to be implanted in the body can be employed.

Figure 2:
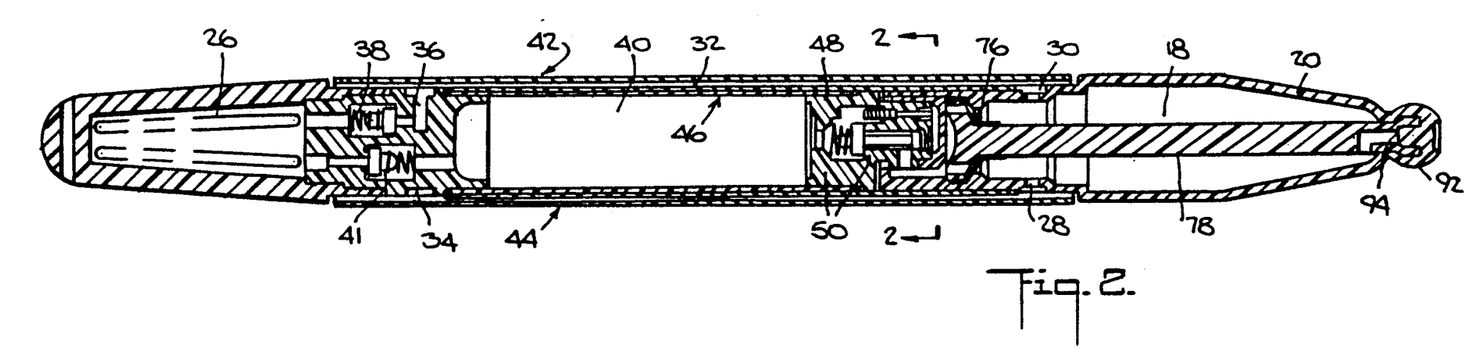
FIG. 2 is a preferred implantable penile prosthesis in accordance with this invention illustrated in a longitudinal cross-sectional view, with the deflation valve in closed mode.

The device 10 depicted in FIG. 1, includes a proximal portion 12, a medial portion 14, and a distal portion 16. In the enlarged cross-sectional view of the device 10, as shown in FIG. 2, the proximal section 12 defines a rear reservoir 18 and provides, in this embodiment, rigidity for the distal portion regardless of the amount of fluid contained therein. Conveniently, rear tip 20 has a slightly tapered external configuration. A rear tip extender 22 shown in FIG. 1, preferably of the type later described, may be provided to lengthen the device 10, if desired.

The distal portion 16 shown in FIG. 1 advantageously includes a front tip 24 that is preferably substantially rigid, so as to resist buckling when in use in the erect state. Advantageously the tip 24 is rigid in both the erect and flaccid states. Within the distal portion 16 of device 10, there is defined a pump 26, shown in FIG. 2, which typically is of the manually compressible type such as, for example, described in U.S. Pat. No. 4,590,927. As shown in FIG. 2, pump 26 is in fluid communication with reservoir 18 through reservoir outlet hole (or holes if more than one are used) 28, reservoir ring channel 30, longitudinal passageway 32, inlet ring channel 34, inlet hole 36 and inlet check valve 38. The pump 26 is also in fluid communication with pressurizable chamber 40 through outlet check valve 41.

Figure 3:
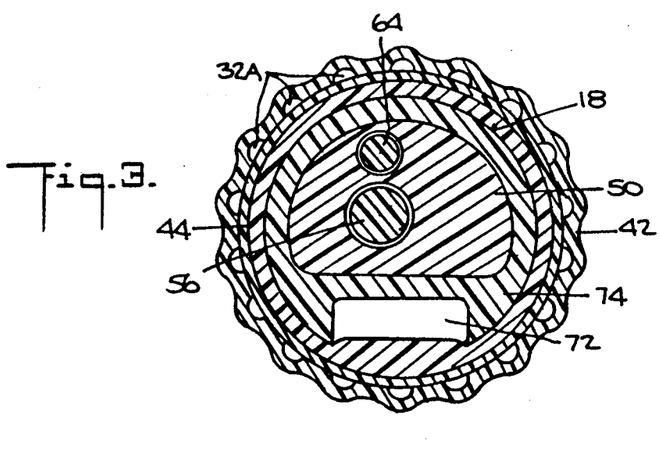
FIG. 3 is a transverse cross-sectional view along the axis 2—2 of the prosthesis of FIG. 2.

The medial portion 14 defines the aforementioned pressurizable chamber 40. This medial portion is positioned along the length of the device 10 so that it is also medially disposed along the length of the corpus cavernosum. Outer layer 42 of said medial portion 14 is preferably comprised of corrugated tubing typically made of a liquid impervious material such as silicone. Concentrically defined within said outer layer 42 is longitudinal passageway 32 (which as indicated in FIG. 3, can be represented as multiple passageways or conduits 32A). Pressurizable chamber 40 is defined interiorly of said passageway 32, and is comprised of two layers, i.e. an inner layer (or bladder) 46 and a substantially non-distensible layer 44 which is disposed concentrically about the inner layer 46. The non-distensible layer 44 may take a variety of forms, but advantageously is formed from a tubular section of woven dacron material, such as a prosthestic vascular graft material. Similarly the inner layer 46 can also take a variety of forms, but advantageously is formed from a tubular section of a liquid impervious material such as silicone.

Located at the end of pressurizable chamber 40 is deflation valve 48, which will be more definitively described hereinafter with reference to FIG. 4 and FIG. 5. Adjacent to the deflation valve 48 is also skirt check valve 76, as later described. These valves are in fluid communication with pressurizable chamber 40 and with each other. While in FIG. 2 both valves are shown on the proximal side of chamber 40, the position of such can be varied.

In the practice of this invention passageway 32 is as stated longitudinally disposed along the length of device 10 between distal portion 16 and proximal portion 12 and serves to convey fluid from the reservoir 18 to the pump 26. It is in fluid isolation with respect to pressurizable chamber 40.

In the preferred embodiment of this invention, passageway 32 is in reality a series of passageways defined as 32A, as shown more clearly in FIG. 3. These passageways are interconnected with each other by means of aforementioned ring channels 34 and 30. The corrugated configuration of outer tubing 42 and the passageways 32A is particularly advantageous in the practice of this invention, because it permits an easier stretching of the medial portion when the device 10 is bent or hinged, which as will be shown later is important to the operation of the device. In other words, the corrugated shape serves to assist the assumption of a flaccid mode because there is virtually no resistance to a circumferential reshaping when the device 10 is hinged in order to assume the flaccid mode. It has also been found that because this configuration re-shapes with a minimum of force, stress upon the silicone of the outer tubing is reduced with improvement in the friction-caused wear-time of said silicone.

As previously mentioned, a vexing problem with most known penile implants is their failure to resume the flaccid condition with a minimum of effort and a maximum (or near maximum) of certainty. The unitary prosthesis defined in FIG. 2, contains many elements which are previously known, such as are described in U.S. Pat. No. 4,590,927, e.g. the stiff distal section including a pump therewithin, the medial section containing a pressurizable chamber capable of being squeezed or bent, and a proximal section defining a reservoir therewithin. However, a unique feature of the subject invention, as illustrated in the prosthesis of FIG. 2, is deflation valve 48 which is fully illustrated in FIG. 4, in its closed mode. This valve provides a quick and sure means (and method) for effecting a quick and sure return of the penis containing the penile implant from the erect to flaccid state.

Figure 4:
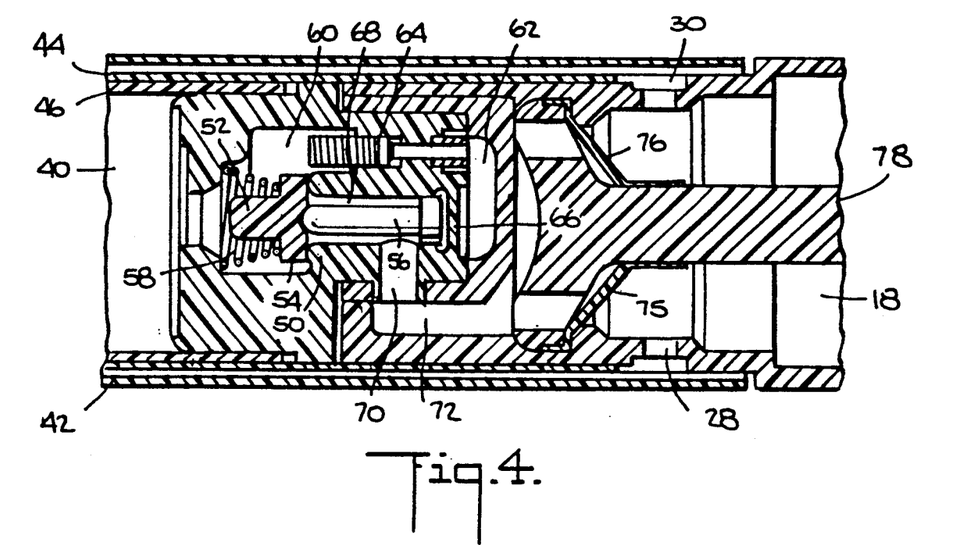
FIG. 4 is an enlarged longitudinal cross-sectional view of the deflation valve shown in FIG. 2, in a closed mode.
Figure 5:
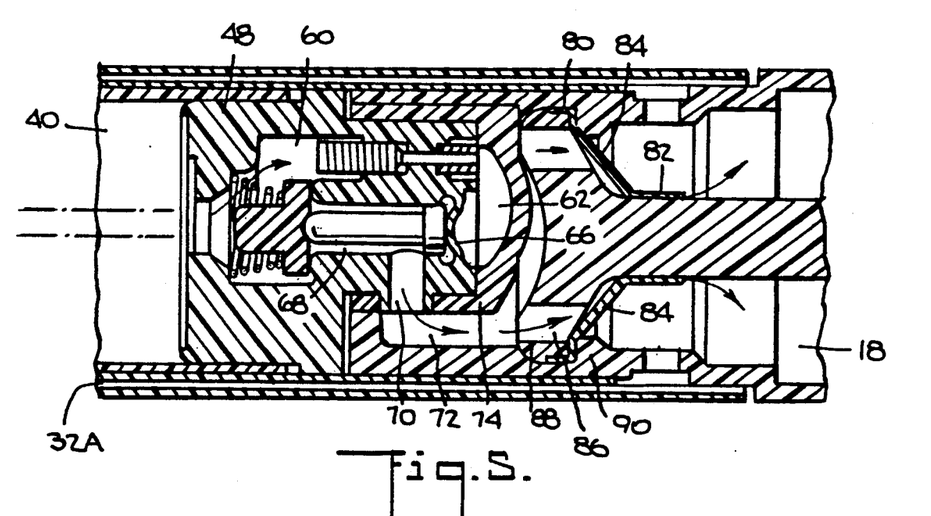
FIG. 5 is an enlarged longitudinal cross-sectional view of the deflation valve shown in FIG. 2, in an open mode.

As shown in FIG. 4, deflation valve 48 which operates on a pressure differential basis, includes a housing 50. In abutting sealing relationship (when the valve is in a closed position which is the normal mode thereof) with said housing is a poppet 52 which preferably comprises a head 54 and a shaft 56. Poppet head 54 is typically held in sealing contact with housing 50 by means of precalibrated spring 58 and also by the fluid pressure exerted by the fluid in the front chamber 60 which is in constant fluid communication with the pressurized chamber. To the rear of the poppet shaft 56 is a rear chamber 62. When the prosthetic device is either in the flaccid or erect mode, the pressure in front chamber 60 and rear chamber 62 is the same. Front chamber 60 and rear chamber 62 are in fluid communication with each other through fluid resistor means 64. The latter provides a predetermined time-deferred resistance to fluid flow to and from front chamber 60 and rear chamber 62. This element 64 may be of several types known in the art, but typically is one of the kind which defines a labyrinth type fluid passage such as one formed by a plurality of axially aligned, perforated disks which are adapted to define a restrictive path for fluid flow.

An important feature of the valve 48 is a movable or distensible partition 66, which is preferably made in the form of a diaphragm. It is preferably spaced apart from and to the rear of poppet shaft 56. Partition 66 is designed to impact upon the poppet shaft when the pressure in rear chamber 62 is sufficiently high. If said pressure is sufficiently high, the necessary extent of which is preset and predetermined, the partition 66 will distend and impact upon the poppet shaft with sufficient force to break the sealing contact of the poppet head 54 with the housing, thereby opening the valve 48. This open mode is shown in FIG. 5, with the lines of flow indicated therein. Fluid is allowed to pass from the pressurizable chamber 40 to the reservoir 18 through a fluid communication line formed by middle chamber 68, outlet hole 70 and fluid passage channel 72. Middle chamber 68 is, as shown, disposed about the poppet shaft medial to the front chamber 60 and rear chamber 62.

FIG. 3, as shown, depicts a transverse cross-sectional view along the axis 2—2 of FIG. 2 through the deflation valve 48. This figure shows the relative disposition of the corrugated outer layer 42 and the multiplicity of passageways, represented by 32A, (also referred to previously as passageway 32 with respect to the medial portion 14). Also shown in this figure is the non-distensible layer 44 referred to with respect to pressurizable section 40, which layer extends into and is fixed onto the outer surface of the housing 50 of deflation valve 48. It also extends to the external surface of the front end of the reservoir 18 and is also affixed thereto. FIG. 3 also shows some of the features of deflation valve 48, in cross-section, to wit: housing 50, pressure cap 74, poppet shaft 56, resistor 64 and fluid passage channel 72.

To prevent spontaneous inflation of the pressurizable chamber 40 by (unintended) transfer of fluid from the reservoir 18 to the chamber 40 through the deflation valve 48, a skirt check valve 76, can be employed. This valve is shown in FIG. 2, FIG. 4 and FIG. 5. This valve is formed of a skirt 75 assembled about a stiffener 78. The skirt, preferably made of silicone, comprises two cylindrical parts as shown, i.e. front part 80 and rear part 82 which are combined by a conical transition 84. When deflation valve 48 is in the open mode, as shown in FIG. 5, fluid from pressurizable chamber 40 flows into the skirt 75 via fluid passage channel 72 and holes 86 of stiffener 78. The pressure differential between pressurized chamber 40 and reservoir 18 allows fluid to stretch the walls of the rear skirt cylinder 82 thus forming a gap between stiffener 78 and the inside walls of skirt rear cylinder 82 for fluid flow to the reservoir 18. The compression fit between the walls of the rear skirt cylinder 82 and stiffener 78 prevents fluid flow from reservoir 18 via the skirt check valve to the pressurized chamber 40. Any pressure increase in the reservoir 18 proportionally increases the compression fit between the skirt rear cylinder and the stiffener. To prevent leaks around the stiffener flange 88, the skirt front cylinder part is glued to a reservoir ring 90.

Figure 6:
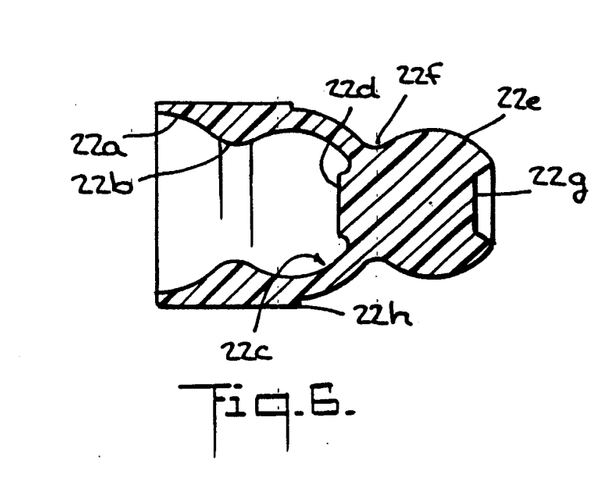
FIG. 6 is an enlarged longitudinal cross-sectional view of a snap rear tip extender, as an optional feature of the penile prosthesis of FIG. 2.

FIG. 6 depicts an optional snap fit rear tip extender (hereinafter to be termed "SRTE") which permits an easy and safe manner for extending the length of the prosthetic device of this invention. The SRTE includes a plug at one end and a receptacle at the other. As shown in FIG. 6, the SRTE receptacle comprises a guide 22a, snap ring 22b, distensible cavity 22c, and a knob 22d. The plug comprises a sphere 22e, neck 22f, recess 22g and step 22h. During assembly with a prosthetic device or with another SRTE, the guide 22a directs a SRTE on to a plug 92, shown in FIG. 2, which has the same geometry as the SRTE plug, or on to the plug end of a SRTE previously attached to the device 10. The ring 22b snaps around the neck 22f, providing a holding force. The knob 22d nests in recess 22g and, with the walls of cavity 22c stretched round the sphere 22e prevents the SRTE from bending and twisting relative to each other or to the prosthetic device. This optional feature permits virtually any length adjustment (normally with 5 mm increments), and for any device diameter. There is accordingly also a predetermined holding force for the SRTE. The SRTE of this embodiment does not increase the diameter of the proximal end of a prosthetic device and can be put on or off as many times as required.

The prosthetic device according to the preferred embodiment of this invention operates as follows: Initially a sufficient amount of fluid is loaded into the reservoir 18 and the pressurizable tubular chamber 40, in any suitable manner, such as for example, the procedure described in U.S. Pat. No. 4,590,927 or by using septum 94 shown in FIG. 2. The prosthesis is then implanted within the corpus cavernosum of the patient utilizing conventional surgical techniques well known in the implantation of penile prosthetic devices. Rear tip extenders, such as the SRTE described above, can be employed to achieve a correct fit.

To operate the device after implantation, the user initially compresses the manually compressible pump 26 externally of the penis. If the pump is in the distal section, it is the tip of the penis that is compressed. The compression of the manually compressible pump 26 forces any fluid contained within the pump into the pressurizable chamber 40. This is because the pressure increase within the pump 26 forces the valve 41 open allowing fluid to flow through the valve. Spring operated inlet check valve 38 remains closed because of the pressure exerted by the compression of the pump 26.

Each time the user releases the pump 26, its walls return back to their original position. The outlet valve 41 is accordingly closed. This creates suction within the pump 26, thus opening the valve 38, and drawing fluid into the pump 26 from reservoir 18. The fluid is drawn from the reservoir 18 through the passageways 32A, inlet channel 34, and inlet hole 36 throughout now open valve 38. When the suction subsides, the valve 38 springs closed. The user may continue to successively depress the pump until the chamber 40 becomes sufficiently pressurized so that the device 10 is in the erect state.

To resume the flaccid state after erection, part of the fluid from the pressurizable chamber 40 has to be transferred back to the reservoir 18. In accordance with this invention, this is done through the deflation valve 48. As discussed above, deflation valve 48 is normally in a closed mode as shown in FIG. 4 due to the compression force of the spring 58 and, when pressurized, the pressure of the front chamber 60. As also discussed, the fluid pressure in the front chamber 60 and rear chamber 62 of the deflation valve 48 is the same as in the pressurizable chamber 40, when the device 10 is in a flaccid or erect position.

In accordance with this invention, to deflate the implanted prosthesis, the user initially bends the penis somewhere along the pressurizable chamber 40, up or down, to or slightly less than a predetermined minimum angle which is typically established by the manufacturer of the prosthesis. For example, the angle can be set for operation at 50°-60° up or down from the original plane. However, the exact angle to be utilized is within the confines of practicality and user convenience. When the penis is bent to the deflation angle the fluid pressure in the pressurizable chamber 40 and in the front chamber 60 of the deflation valve 48, which is in fluid communication with the chamber 40, is increased. The fluid pressure in the rear chamber 62 of the deflation valve will also increase and will become equal to the increased fluid pressure of the front chamber 60 and the pressurizable chamber 40. This will occur, however, after a short time delay caused by the time-deferred passage of fluid from the front chamber to the rear chamber through the fluid resistor 64. The time delay (which can be predetermined) required to equalize pressure in chamber 40 and chambers 60 and 62, depends on the flow configuration of fluid resistor 64, the pressure differential between the front and rear chambers shortly after the penis is bent to the deflation angle, and the compliance of the rear chamber 62, i.e. the ease with which the latter will expand under pressure. The increased pressure in the rear chamber (while the same as that of the front chamber) still deflects the distensible partition or diaphragm 66 towards the poppet 56. This deflection is directly proportional to the rear chamber pressure and to the diameter of the diaphragm, and is inversely proportional to the thickness of the diaphragm However, at this point the sealing compression of the poppet head is still not affected because the pressures, though increased in both chambers, are still the same in all of those chambers.

After the predetermined time delay has expired, the user brings the penis back to the straight position abruptly. (Parenthetically, it must be stressed that the "time delays" referred to are measured in seconds, e.g. on the order of 5-10 seconds). When the penis is abruptly returned to the straight position, the fluid pressure in the pressurizable chamber 40 and the front chamber 60 almost immediately returns to the initial level (i.e. to that level before the penis was bent to the deflation angle). However, the fluid pressure of the rear chamber 62 will not return to the initial pressure as quickly, i.e. it will remain higher for some time, (measured again in seconds) because the return flow of fluid from the rear chamber 62 to the front chamber 60 is again time-deferred because of the fluid resistor 64. Until this is done, there is thus a pressure differential between the front and rear chambers. Now the higher pressure of the rear chamber causes the already deflected diaphragm 66 to impact upon the poppet 52. The latter is thereby pushed off its sealing contact with the valve housing, thus opening the deflation valve. The valve accordingly stays open until the pressure is equalized in the chamber 40 and in chambers 60 and 62. As previously described while the deflation valve 48 is open, fluid from the pressurizable chamber 40 flows to the reservoir 18 (because the latter has a lower pressure after the erect state has been induced). This is done through the communication conduit formed by the middle chamber 68, outlet hole 70, fluid passage channel 72, holes 86 in the stiffener flange 88, and the skirt check valve 76.

However, while less desirable, it is also possible to operate the deflation valve of this invention, and accordingly to change the prosthetic device of this invention from the erect to the flaccid state, without bending the penis to the deflation angle. Illustratively this could be done by directly increasing the pressure of the rear chamber of the deflation valve by, for example, adding pressurized fluid from an outside source such as an implantable squeezable bulb filled with fluid which is connected by tubing or other suitable means directly to the rear chamber. In this manner the pressure differential sequence, as defined above, could still occur within the valve. This might be advantageous to those users who have difficulty in bending or squeezing the penis.

It is also possible, although again less desirable, for the pressure conditions which will open the deflation valve to not require that the pressure of the rear chamber of the valve be higher than that of the front chamber. In this embodiment, the same, or essentially the same, pressure in the rear chamber can impact with sufficient force on the poppet to cause the valve to assume an open mode, if the area of the wall of the movable or distensible partition is sufficiently larger than the area of the poppet head. The same time deferred sequence will then still serve to shift the pressures from the front to rear chamber. However, because the force exerted will be proportional to the area of the partition as well as the pressure of the rear chamber, the latter pressure need not be greater than that of the front chamber to cause the distensible or movable partition to impact upon the poppet with sufficient force to cause the latter to break sealing contact with the valve housing.

It is also apparent that modifications and variations besides those specifically mentioned herein may be made in the structures and techniques described herein and depicted in the accompanying drawings without departing from the concept of the present invention. For example, while the deflation valve of this invention is depicted as being primarily applicable to implantable penile prosthetic systems, it can also be used in conjunction with any hydraulic device where sure and quick deflation is needed or is desirable.

We claim:

1. A penile prosthesis implantable within at least one corpus cavernosum of the penis, said prosthesis comprising:
   an implantable broadly tubular enclosure;
   a generally tubular pressurizable chamber section defined within said enclosure, said chamber section being transformable from a flaccid to an erect state, and which is capable of being squeezed or bent; and a deflation valve for returning said chamber section from the erect to flaccid state, said valve being in fluid communication with said tubular pressurizable chamber section and with a fluid reservoir, said valve comprising closure means for normally keeping the valve in a closed mode, means for time-deferring the transfer of fluid within said valve thereby effecting a change in the internal pressure conditions within said valve, and a movable partition disposed within a distensible chamber within said valve capable of exerting sufficient force upon said closure means, as a consequence of said change in internal pressure conditions, to place said valve in an open mode.

2. A deflation valve for a hydraulic system comprising closure means for normally keeping the valve in a closed mode, means for time-deferring the transfer of fluid within said valve thereby effecting a change in the internal pressure conditions within said valve, and a movable partition disposed within a distensible chamber within said valve capable of exerting sufficient force upon said closure means, as a consequence of said change in internal pressure conditions, to place said valve in an open mode.

3. A deflation valve for a hydraulic system comprising a housing having defined therewithin:
   closure means comprising a poppet and including means for exerting a force upon the head of said poppet for normally keeping the sealing edge thereof in sealing contact with in inner surface of said housing;
   said poppet head being disposed within a chamber containing fluid, the fluid pressure in said chamber and said means for exerting a force upon said poppet head normally keeping the closure means and thereby the valve mechanism in a closed mode;
   a movable partition capable of impacting upon said poppet; and
   a further distensible chamber adjacent to said partition, said chamber being in fluid communication with the chamber disposed about the poppet head through means which time-defer the transfer of fluid between said chambers; whereby, under precalibrated pressure conditions, fluid pressure in said further chamber will distend said partition to exert sufficient force upon said poppet to break the sealing contact of said poppet head with said housing, thereby placing the valve mechanism in an open mode.

4. A valve mechanism according to claim 3, wherein the precalibrated pressure differential conditions which result in placing said valve mechanism in an open mode occur as a consequence of a prescribed initial sharp increase in the fluid pressure of the chamber disposed about the poppet head followed by a prescribed sharp decrease in the fluid pressure of said chamber, whereby because of the time-delay occasioned by the means which transfers the flow of fluids to and from said chamber to the chamber disposed adjacent to the partition, the pressure of the latter chamber will be differentially higher than that of the chamber disposed about the poppet head thereby distending the partition and causing ti to impact upon the poppet in such manner as to open said valve mechanism.

5. A pressure differential valve mechanism for a hydraulic system comprising a housing having defined therewithin:
   closure means comprising a poppet and including means for exerting a force upon the head of said poppet for normally keeping the sealing edge thereof in sealing contact with the inner surface of said housing;
   said poppet head being disposed within a chamber containing fluid, the fluid pressure in said chamber and said means for exerting a force upon said poppet head normally keeping the closure means and thereby the valve mechanism in a closed mode;
   a distensible partition capable of impacting upon said poppet; and
   a further distensible chamber adjacent to said distensible partition, said chamber being in fluid communication with the chamber disposed about the poppet head through means which time-defer the transfer of fluid between said chambers; whereby, under precalibrated pressure differential conditions fluid pressure in said further chamber will distend said partition to exert sufficient force upon said poppet to break the sealing contact of said poppet head with said housing, thereby placing the valve mechanism in an open mode.

6. A valve mechanism according to claim 5, wherein the means for exerting a force upon said poppet head is a precalibrated spring and wherein said poppet includes a shaft.

7. A valve mechanism according to claim 6, wherein said poppet shaft is defined within a chamber disposed about said shaft, said chamber not being normally in fluid communication with said chamber disposed about the poppet head, said chamber about the poppet shaft containing outlet means therein for the passage of fluid out of said valve mechanism.

8. A valve mechanism according to claim 7, wherein said distensible partition is normally spaced apart from and to the rear of said poppet shaft.

9. A value mechanism according to claim 7, wherein said further chamber is disposed to the rear of said distensible partition.

10. A valve mechanism according to claim 5, wherein the hydraulic system is a body implantable system which includes a generally tubular pressurizable chamber section capable of being squeezed or bent which is in fluid communication with a fluid reservoir for said hydraulic system.

11. A valve mechanism according to claim 5, wherein the means which time defer the transfer of fluid between the chamber disposed about the poppet head and the chamber disposed adjacent to the distensible partition comprises fluid resistor means.

12. A valve mechanism according to claim 5, wherein the distensible partition is a distensible diaphragm.

13. A pressure differential valve mechanism for a body implantable hydraulic system comprising a housing having defined therewithin:
- closure means comprising a poppet having a head and shaft and a precalibrated spring for exerting a force upon said poppet head thereby normally keeping the sealing edge of said poppet head in sealing contact with the inner surface of said housing;
- said poppet head being disposed within a front chamber containing fluid, the fluid pressure in said chamber and said precalibrated spring normally keeping the closure means and thereby the value mechanism in a closed mode;
- a distensible diaphragm spaced apart from and to the rear of said poppet shaft which when sufficient pressure is applied thereto will impact upon said poppet shaft;
- a distensible rear chamber disposed to the rear of said diaphragm, said chamber being in fluid communication with the front chamber through fluid resistor means which are capable of effecting a time-deferred transfer of fluid between said front and rear chambers; and
- a chamber disposed about the poppet shaft, which chamber is not normally in fluid communication with said front chamber disposed about the poppet head, said chamber disposed about the poppet shaft containing outlet means therein for the passage of fluid out of said valve mechanism; whereby under precalibrated pressure differential conditions the fluid pressure in said rear chamber will distend said diaphragm to exert sufficient force upon said poppet to break the sealing contact to said poppet head with said housing, thereby opening the valve mechanism and allowing fluid to pass into the chamber disposed about the poppet shaft and out of the outlet means contained therein.

14. A penile prosthesis implantable within at least one corpus cavernosum of the penis, said prosthesis comprising:
- an implantable broadly tubular enclosure;
- a generally tubular pressurizable chamber section defined within said enclosure, said chamber section being transformable from a flaccid to an erect state, and which is capable of being squeezed or bent; and
- a deflation valve for returning said chamber section for the erect to flaccid state, said valve being in fluid communication with said tubular pressurizable chamber section and with a fluid reservoir, said valve comprising a housing having defined therewithin:
  - closure means comprising a poppet having a head and shaft, and including means for exerting a force upon said poppet head for normally keeping the sealing edge thereof in sealing contact with the inner surface of said housing;
  - said poppet head being disposed within a chamber containing fluid, said chamber being in fluid communication with said tubular pressurizable chamber section, the fluid pressure in said chamber and said means for exerting a force upon said poppet head normally keeping the closure means and thereby the valve mechanism in a closed mode;
  - a movable partition capable of impacting upon said poppet; and
  - a further distensible chamber adjacent to said partition, said chamber being in fluid communication with the chamber disposed about the poppet head through means which time-defer the transfer of fluid between said chambers; whereby, under precalibrated pressure conditions fluid pressure in said further chamber will distend said partition to exert sufficient force upon said poppet to break the sealing contact of said poppet head with said housing, thereby placing the valve mechanism in an open mode, whereby fluid from said tubular pressurizable chamber section will flow into the chamber disposed about the poppet head and then into said fluid reservoir thereby deflating said tubular chamber section and returning said section to its flaccid state.

15. A penile prosthesis according to claim 14, wherein to effect said precalibrated pressure differential conditions within the deflation valve the pressurizable chamber section is initially bent to a predetermined extent so that the fluid pressure in the chamber disposed about the poppet head is sharply increased, and is then quickly returned to its unbent position so that the fluid pressure in the chamber disposed about eh poppet head is sharply decreased back to its original pressure, but wherein because of the time-delay occasioned by the means which transfers the flow of fluids to and from said latter chamber to the chamber disposed adjacent to the distensible partition, the pressure of the latter chamber is differentially higher than that of the chamber disposed about the poppet head, said higher pressure thereby distending the partition and causing it to impact upon the poppet thereby opening said deflation valve.

16. A penile prosthesis implantable within at least one corpus cavernosum of the penis, said prosthesis comprising:
- an implantable broadly tubular enclosure;
- a generally tubular pressurizable chamber section defined within said enclosure, said chamber section being transformable from a flaccid to an erect state, and which is capable of being squeezed or bent; and disposed about the poppet head, said chamber disposed about the poppet shaft containing outlet means therein for the passage of fluid out of said valve mechanism; whereby under precalibrated pressure differential conditions the fluid pressure in said rear chamber will distend said diaphragm to exert sufficient force upon said poppet shaft to break the sealing contact of said poppet head with said housing, thereby opening the valve mechanism and allowing fluid to pass into the chamber disposed about the poppet shaft and out of the outlet means contained therein.

17. A penile prosthesis according to claim 16, wherein said tubular pressurizable chamber section is transformable from its flaccid to its erect state when the interior volume thereof is filled substantially to capacity, and wherein pump means are provided in fluid communication with said tubular chamber section, said pump means being adapted to pump fluid to said chamber section so that the volume of said chamber section increases as it changes from its flaccid to its erect state.

18. A unitary penile prosthesis implantable within at least one corpus cavernosum of the penis, said prosthesis comprising:
 an implantable, broadly tubular enclosure:
  a generally tubular pressurizable chamber section defined medially within said enclosure, said chamber section including a substantially nondistensible tubular portion and a tubular sleeve concentric with said tubular portion, said tubular portion being transformable from a flaccid to an erect state when the interior volume of said tubular portion is filled substantially to capacity;
 a fluid containing reservoir defined within said enclosure in series along the length of said enclosure with respect to said chamber section; a manually compressible pump defined within said enclosure in series along the length of said enclosure with respect to said chamber section, said pump adapted for fluid communication with said tubular portion, said reservoir and said pump being located on opposite sides of said chamber section;
 a deflation valve for returning said chamber section from the erect to flaccid state, said valve being in fluid communication with said tubular pressurizable chamber section and with a fluid reservoir, said valve comprising a housing having defined therewithin;
 closure means comprising a poppet having a head and shaft, and a precalibrated spring for exerting a force upon said poppet head thereby normally keeping the sealing edge of said poppet head in sealing contact with the inner surface of said housing;
 said poppet head being disposed within a front chamber containing fluid, said chamber being in fluid communication with said tubular pressurizable chamber section, the fluid pressure in said chamber and said precalibrated spring normally keeping the closure means and thereby the valve mechanism in a closed mode;
 a distensible diaphragm spaced normally apart from and to the rear of said poppet shaft which when sufficient pressure is applied thereto will impact upon said poppet shaft;
 a distensible rear chamber disposed to the rear of said diaphragm, said chamber being in fluid communication with the front chamber through fluid resistor means which are capable of effecting a time-deferred transfer of fluid between said front and rear chambers; and
 a chamber disposed about the poppet shaft, which chamber is not normally in fluid communication with said front chamber
 a passageway fluidically connecting said reservoir and said pump, said passageway being maintained in fluid isolation from said chamber section, said pump adapted to pump fluid to said tubular portion from said reservoir such that the volume of said chamber section increases as said chamber section is transformed from its flaccid to its erect state; and
 a pressure differential deflation valve for returning said chamber section from the erect to the flaccid state, said valve being in fluid communication with said chamber section and said reservoir, said valve comprising a housing having defined therewithin:
  closure means comprising a poppet and including means for exerting a force upon the head of said poppet for normally keeping the sealing edge thereof in sealing contact with the inner surface of said housing;
  said poppet head being disposed within a chamber containing fluid, said chamber being in fluid communication with said tubular pressurizable chamber section, the fluid pressure in said chamber and said means for exerting a force upon said poppet head normally keeping the closure means and thereby the valve mechanism in a closed mode;
  a distensible partition capable of impacting upon said poppet; and
  a further chamber adjacent to said distensible partition, said chamber being in fluid communication with the chamber disposed about the poppet head through means which time-defer the transfer of fluid between said chambers; whereby, under precalibrated pressure differential conditions fluid pressure in said further chamber will distend said partition to exert sufficient force upon said poppet to break the sealing contact of said poppet head with said housing, thereby placing the valve mechanism in an open mode.

19. A unitary penile prosthesis according to claim 18, wherein the means for exerting a force upon said poppet head of said deflation valve is a precalibrated spring and wherein said poppet includes a shaft defined within a chamber disposed about said shaft, said chamber not being normally in fluid communication with said chamber disposed about the poppet head, said chamber about the poppet shaft containing outlet means therein for the passage of fluid out of said valve.

20. A unitary penile prosthesis according to claim 19, wherein said distensible partition of said valve is normally spaced apart from and to the rear of said poppet shaft whereupon when sufficient pressure is applied said partition will impact upon said poppet shaft and wherein said further chamber is disposed to the rear of said distensible partition.

21. A unitary penile prosthesis according to claim 20, wherein the means which time-defer the transfer of fluid between the chamber disposed about the poppet head and the further chamber disposed adjacent to the distensible partition comprises fluid resistor means, and the distensible partition is a distensible diaphragm.

22. A unitary penile prosthesis implantable within at least one corpus cavernosum of the penis, said prosthesis comprising:
 an elongated front portion for mounting inside the distal portion of a patient's penis, said front portion comprising a cylinder which is substantially rigid;
 a proximal, rearward portion adapted to be implanted within the root end of the penis, said rearward portion containing a fluid reservoir;
 a medial portion defined between said front and rearward portions, said medial portion defining a generally tubular pressurizable chamber section, said chamber section including a substantially non-distensible tubular portion and a tubular sleeve concentric with said tubular portion, said tubular portion being transformable from a flaccid to an erect, stiff state when the interior volume of said tubular portion is filled substantially to capacity, said fluid reservoir being in series along the length of said prosthesis with respect to said chamber section;

a manually compressible pump defined within said front portion and also in series along the length of said prosthesis with respect to said chamber section, said pump also being in fluid communication with said tubular portion;

a longitudinal passageway fluidically connecting said reservoir and said pump, said passageway being maintained in fluid isolation from said chamber section, said pump adapted to pump fluid to said tubular portion from said reservoir such that the volume of said chamber section increases as said chamber section is transformed from its flaccid to its erect state; and a pressure differential deflation valve for returning said chamber section from the erect to the flaccid state, said valve being in fluid communication with said chamber section and said reservoir, said valve comprising a housing having defined therewithin:

closure means comprising a poppet and including means for exerting a force upon the head of said poppet for normally keeping the sealing edge thereof in sealing contact with the inner surface of said housing;

said poppet head being disposed within a chamber containing fluid, said chamber being in fluid communication with said generally tubular pressurizable chamber section, the fluid pressure in said chamber and said means for exerting a force upon said poppet head normally keeping the closure means and thereby the valve mechanism in a closed mode;

a distensible partition capable of impacting upon said poppet; and a further chamber adjacent to said distensible partition, said chamber being in fluid communication with the chamber disposed about the poppet head through means which time-defer the transfer of fluid between said chambers; whereby, under precalibrated pressure differential conditions fluid pressure in said further chamber will distend said partition to exert sufficient force upon said poppet to break the sealing contact of said poppet head with said housing, thereby placing the valve mechanism in an open mode.

23. A unitary penile prosthesis according to claim 22, wherein the means for exerting a force upon said poppet head of said deflation valve is a precalibrated spring and wherein said poppet includes a shaft defined within a chamber disposed about said shaft, said chamber not being normally in fluid communication with said chamber disposed about the poppet head, said chamber about the poppet shaft containing outlet means therein for the passage of fluid out of said valve.

24. A unitary penile prosthesis according to claim 23, wherein said distensible partition of said valve is normally spaced apart from and to the rear of said poppet shaft whereupon when sufficient pressure is applied said partition will impact upon said poppet shaft and wherein said further chamber is disposed to the rear of said distensible partition.

25. A unitary penile prosthesis according to claim 24, wherein the means which time defer the transfer of fluid between the chamber disposed about the poppet head and the further chamber disposed adjacent to the distensible partition comprises fluid resistor means, and the distensible partition is a distensible diaphragm.

26. A unitary prosthesis according to claim 22, wherein an outer layer of said medial portion comprises a corrugated tubing.

27. A unitary prosthesis according to claim 26, wherein said longitudinal passageway fluidically connecting said reservoir and said pump comprises a series of conduits fluidically interconnected with each other and defined concentrically inside of said corrugated outer layer of said medial portion.

28. A unitary prosthesis according to claim 27, wherein a skirt check valve is disposed rearward to said deflation valve to prevent spontaneous inflation of the pressurizable chamber section by the unintended transfer of fluid from the reservoir to said chamber section through said deflation valve.

29. A unitary prosthesis according to claim 22, wherein at least one detachable tip extender having snap fit means is attached to the proximal rearward portion of the prosthesis or to the end of a tip extender already snap fitted to said end of said proximal rearward portion.

30. A method for deflating a penile prosthesis implanted within at least one corpus cavernosum so as to return said prosthesis from its erect to its flaccid state, said prosthesis having an implantable broadly tubular enclosure; and a generally tubular pressurizable chamber section defined within said enclosure, said chamber section being transformable from a flaccid to an erect state and being capable of being squeezed or bent;

which method comprises providing:

a deflation valve which is in fluid communication with said tubular chamber section and with a fluid reservoir, said valve comprising a housing having defined therewithin:

closure means comprising a poppet and including means for exerting a force upon the head of said poppet for normally keeping the sealing edge thereof in sealing contact with the inner surface of said housing;

said poppet head being disposed within a chamber containing fluid, said chamber being in fluid communication with said generally tubular pressurizable chamber section, the fluid pressure in said chamber and said means for exerting a force upon said poppet head normally keeping the closure means and thereby the valve mechanism in a closed mode;

a distensible partition capable of impacting upon said poppet; and a further chamber adjacent to said distensible partition, said chamber being in fluid communication with the chamber disposed about the poppet head through means which time-defer the transfer of fluid between said chambers; whereby, under precalibrated pressure differential conditions fluid pressure in said further chamber will distend said partition to exert sufficient force upon said poppet to break the sealing contact of said poppet head with said housing, thereby placing the valve mechanism in an open mode;

bending the penis up or down in the body plane to or below a predetermined minimum deflation angle, thereby increasing the pressure of the pressurizable chamber section and the chamber in said deflation valve about the poppet valve, the chamber in said deflation valve adjacent to said distensible partition also then obtaining an equally increased pressure after a predetermined time delay; and returning the penis suddenly back to its straight position, which immediately reduces the pressure in the pressurizable chamber section and in the chamber in said deflation valve about the poppet head back to its initial level, the pressure in the chamber adjacent to said distensible partition thereby remaining higher than the pressure in the aforesaid two chambers for a period of time dependent on the means which time-defer the transfer of fluid between said chambers, so that said higher pressure distends the distensible partition with sufficient force to break the sealing contact of the poppet head with the valve housing, thereby opening said valve and permitting the flow of fluid from the pressurizable chamber section into said reservoir, thereby equalizing the pressure in all chambers and effecting the deflation of the prosthesis.

* * * * *

UNITED STATES PATENT AND TRADEMARK OFFICE
CERTIFICATE OF CORRECTION

PATENT NO. : 5,010,882
DATED : April 30, 1991
INVENTOR(S) : Mark Polyak, Robert W. Pugh Jr.

It is certified that error appears in the above-identified patent and that said Letters Patent is hereby corrected as shown below:

Claim 16, column 12, insert in line 51, before the word "disposed":

-- a deflation valve for returning said chamber section from the erect to flaccid state, said valve being in fluid communication with said tubular pressurizable chamber section and with a fluid reservoir, said valve comprising a housing having defined therewithin;

closure means comprising a poppet having a head and shaft, and a precalibrated spring for exerting a force upon said poppet head thereby normally keeping the sealing edge of said poppet head in sealing contact with the inner surface of said housing;

said poppet head being disposed within a front chamber containing fluid, said chamber being in fluid communication with said tubular pressurizable chamber section, the fluid pressure in said chamber and said precalibrated spring normally keeping the closure means and thereby the valve mechanism in a closed mode;

a distensible diaphragm spaced normally apart from and to the rear of said poppet shaft which when sufficient pressure is applied thereto will impact upon said poppet shaft;

a rear chamber disposed to the rear of said diaphragm, said chamber being in fluid communication with the front chamber through fluid resistor means which are capable of effecting a time-deferred transfer of fluid between said front and rear chambers; and

UNITED STATES PATENT AND TRADEMARK OFFICE
CERTIFICATE OF CORRECTION

PATENT NO. : 5,010,882

DATED : April 30, 1991

INVENTOR(S) : Mark Polyak, Robert W. Pugh Jr.

It is certified that error appears in the above-identified patent and that said Letters Patent is hereby corrected as shown below:

a chamber disposed about the poppet shaft, which chamber is not normally in fluid communication with said front chamber --

Signed and Sealed this

Sixth Day of April, 1993

*Attest:*

STEPHEN G. KUNIN

*Attesting Officer*      *Acting Commissioner of Patents and Trademarks*